United States Patent [19]

Jansa et al.

[11] Patent Number: 4,900,447

[45] Date of Patent: Feb. 13, 1990

[54] METHOD FOR DETERMINATION OF MUCOPROTEIN VECTOR

[75] Inventors: Jaroslav Jansa, Slusovice; Peter Urbänek, Trencin; Milos Cesal, Trencin; Karel Bitto, Trencin, all of Czechoslovakia

[73] Assignee: Jednotne zemedelske druzstvo, Abrokombinat Slusovice, Czechoslovakia

[21] Appl. No.: 64,150

[22] Filed: Jun. 18, 1987

[30] Foreign Application Priority Data

Jun. 18, 1986 [CS] Czechoslovakia .................... 4514-86

[51] Int. Cl.⁴ ............................................. B01D 15/08
[52] U.S. Cl. ..................................... 210/635; 210/656; 436/86; 436/87; 530/380; 530/395; 530/416
[58] Field of Search ...................... 210/635, 656, 198.2, 210/659; 436/86, 87; 530/380, 395, 416

[56] References Cited

FOREIGN PATENT DOCUMENTS 238020 11/1985 Czechoslovakia .................. 210/635

OTHER PUBLICATIONS

Computer Printout Evidencing Publication Date.
Salas, *Calculus One and Several Variables* Third Edition, John Wiley & Sons, New York, 1978.

Primary Examiner—Ernest G. Therkorn
Attorney, Agent, or Firm—Klein & Vibber

[57] ABSTRACT

Method for determination of mucoprotein vector from blood serum and its eluates through separation of the blood serum mucoproteins by means of gel ion-exchanger chromatography into at least two subgroups, through determination of mucoprotein concentration in the whole serum and in the two subgroups and through transfer of the obtained concentration values to x, y, and z axes.

1 Claim, 1 Drawing Sheet

METHOD FOR DETERMINATION OF MUCOPROTEIN VECTOR

FIELD OF THE INVENTION

This invention concerns a method for determination and evaluation of the so-called mucoprotein vector of blood serum and its eluates.

DESCRIPTION OF THE PRIOR ART

It is a well known fact that various pathological changes in the organism of mammals, especially of man, manifest themselves by qualitative and quantitative alterations of mucoproteins in blood serum. Attempts have already been made to examine and evaluate these alternations, especially in view of a possibility to use the obtained results for diagnosis of tumor diseases. E.g. Mehl (Homomlka J.: Polarografie Bilkovin A Jeji Klinicke Vyuziti, 62–66, 1964 SZN Praha) has divided mucoproteins into three fractions, MP 1, MP 2, and MP 3 occurring in the field of $\alpha_1$-, $\alpha_2$- and $\beta$-globulins. Kalous (Kalous V. : Chem. listy 48, 747, 1964) has proved that carcinomata increase the MP 1 fraction. The fact is corroborated by Winzler (Winzler R. J. Behesi G. Methods in Cancer Research, Vol. 2. 150–202, 1967 Academic Press, New York) that mucoprotein fractions can offer information for diagnosis of tumor diseases. Dermer (Dermer B.C. Silverman M. L., Gendler S. J., Tokes Z. A.: Clin. Chem. Acta 26, 3, 392–395, 1980) concentrated on electroporesis of glycoproteins. He found out that a split in $\alpha_2$ - glycoprotein fraction was specific for various adenocarcinomata. Snyder and Ashwell (Snyder S. Ashwell C. : Clin. Chem. Acta 34, 119–154, 1971) have also examined quantity of mucoprotein in human serum and have found out that the quantity of certain mucoproteins in a carcinoma rises and of some other mucoproteins falls. Some authors have adopted the so-called Brdicka's index (BI) (Homolka J.:Poilarografie Bilkovin A Jeji Klinicke Vyuziti 30–37,d 1964, SZN Praha), for determination of the mucoprotein quantity. But there is no evidence so far of a direct link between BI value and malignant diseases. In "Biochem. Clin. Bohemoslov.", 13, 1984, pp. 115–122 and in Author's Certificate No. 238 020 there is a description of mucoprotein separation in blood serum by chromatography, of determination of polarographical activities of individual fractions and of attempts at individual evaluation of the obtained values with the aim to discover a method for diagnosing tumor diseases. Eventhough the achieved results seem promising, the methods discovered so far do not represent any reliable means for broader practical application.

It has now been discovered that much more exact and reproducible results can be obtained if blood serum mucoproteins are separated into at least two subgroups and if the mucoprotein concentration is determined in the whole serum and in the subgroups. The obtained values are transferred to x, y, and z axes and a point is thus obtained in a three-dimensional space that is specific for the given blood and for the given arrangement of the whole determination and that corresponds to the so-called "mucoprotein vector". (This is valid in case of three concentrations. In the case of n-concentrations, we obtain a point in n-dimensional space).

OBJECT OF THE INVENTION

Thus, the object of the invention is a method for determining the mucoprotein vector from blood serum and its eluates obtained through separation by means of ion-exchager. The principle of the method is that blood serum proteins in the mucoprotein component are separated by means of a gel ion-exchanger chromatography into at least two subgroups, and mucoprotein concentration is then determined respectively in the subgroups and in the whole serum. Individual concentration values are then transferred to x, y, and z axes and a point in space is obtained corresponding to the mucoprotein vector specific for the given blood.

The gel ion-exchanger chromatograph itself is quite well known and generally applied in biochemistry. For the purpose of the invention no modification in equipment and technology or procedures are necessary.

Mucoprotein concentration in the whole serum and in individual subgroups can be determined by various methods, usually it is done by means of polarography but there is no reason why other known methods such as photometry or electrophoresis can not be used.

The obtained values can be transferred to individual axes manually, but because of a greater number of determinations it is advisable to make use of electronic computers equipped with a proper program, which does not represent any problem for a specialist.

This method can be applied to an adequate number of persons with a known diagnosis and thus the given space can be "calibrated". Any following determination will then place the mucoprotein vector into a certain section of the space, which will facilitate in a very simple and exact way the definition of a correct diagnosis of the person under examination.

The method for determining the mucoprotein vector according to this invention has been applied for checking the state of health of patients with the aim to diagnose malignant growths. Results that are about 90% correct have been obtained.

A more detailed description of the application of the method, and of evaluation of the obtained results is described more fully below.

SUMMARY OF THE ADVANTAGES OF THE PRESENT INVENTION

From the above mentioned facts it is evident that the method now disclosed respresents a major improvement in the biochemical methods that can be applied to check the state of health of people, or more specifically to diagnose malignant growths before any clinical symptoms can be discovered. It is a well known fact that early diagnosis of malignant tumors plays a decisive role in the prospect for successful treatments.

Simplicity of the method, according to the invention, would allow for the screening of vast sections of the population under economically acceptable conditions. It could, for example, be introduced on the same scale as present day obligatory X-ray lung screening.

DETAILED DESCRIPTION OF THE INVENTION BY WAY OF PREFERRED EMBODIMENTS

The invention is illustrated with reference to the following preffered examples, which however does not limit the scope of the claimed invention.

EXAMPLE I Composition and preparation of solutions:

1. Basic TRIS-HCl buffer: 50 ml aqueous solution treated by concentrated hydrochloric acid to pH 7.0

2. Elution solution A: as much sodium chloride as is necessary is weighed into the basic buffer to make the resulting Cl⁻ concentration 45-50 mmol/litro.

Elution solution B: as much sodium chloride as is necessary is weighed into the basic buffer to make the resulting Cl⁻ concentration 320-330 mmol/liter.

Elution solution C: as much sodium chloride as is necessary is weighed into the basic buffer to make the resulting Cl⁻ concentration 480-500 mmol/liter.

3. Gel Sephadex DEAE A-50 : 100 ml basic buffer is poured on 1.0g native substance. The buffer forms a liquid layer on the gel. Gel suspension is to be prepared 24 hours in advance and it can be used within a 14-day period. The suspension is to be stored in the refridgerator.

4. 2N ammonia

5. Stock solution of hexaammocobalt trichloride: 0.2675 g [Co(NH$_3$)$_6$]Cl$_3$ and 5.35 g ammonium chloride are to be dissolved in water, distilled water added to make up a 500 ml volume.

6. Brdicka's solution of trivalent cobalt : No. 4 solution is mixed with No. 5 solution. The resulting solution can be used within a month's period.

7. 20% aqueous solution of sulphosalicyclic acid 8. 0.1N aqueous solution of potassium hydroxide Method Using Solutions Of Example I 3.5 ml gel is put into a plastic column (required height of the gel column is marked on the wall of the plastic column in advance). After the last drop of the liquid has been drained off the column, 2 ml elution solution A is poured on the gel surface and is allowed to pass through by gravitation. Afterwards, 0.5 ml serum under examination is put on the gel surface and is allowed to soak into the gel. A beaker marked "eluate A" is placed under the column. First, 1 ml elution solution A is pipetted on the gel surface. Care must be taken not to stir the gel. The solution is allowed to pass through. Then another 3 ml elution solution A is pipetted on the gel surface. After the last drop, eluate A is obtained.

Mostly β- and α- globulins are washed out by elution solution A. This eluate serves only for selective winning of B and C eluates and is not used for further analysis.

A beaker marked "eluate B" is placed under the column. 1 ml elution solution B is pipetted on the gel surface and allowed to pass through. Then another 2 ml elution solution B is pipetted on the gel surface. After the last drop, eluate B is obtained and is stirred thoroughly.

Finally a beaker marked "eluate C" is placed under the column, and 2 ml elution solution C is pipetted on the gel surface. After the last drop, eluate C is obtained and is stirred thoroughly.

0.4 ml serum under examination is pipetted into a test tube marked S, 0.6 ml eluate B is pipetted into a test tube marked E$_{300}$ and 0.6 ml eluate C is pipetted into a test tube marked E$_{500}$. Then 1 ml 0.1N potassium hydroxide solution is added into each of the three test tubes, the contents of the test tube is mixed thoroughly and the test tubes are allowed to stand for 45 minutes. After that time, 1 ml 20% sulphosalicylic acid is added into each of the three test tubes, the contents is stirred thoroughly and allowed to stand for 10 minutes. Then the eliminated precipitates are filtered off. If some of the filtrate is not clear, it must be centrifuged at 5,500-6,000 r.p.m. for 10 minutes, if possible, in a cooled centrifuge at 2° C. From the filtrate of the S test tube 0.2 ml is pipetted off, from the filtrates of the E$_{300}$ and E$_{500}$ test tubes 0.8 ml is pipetted off. 2 ml Brdicka's solution is then added to each of the portions and the resulting solutions are then polarographically examined.

Polarography is carried out within the range of 0.6V -1.6V (formation of protein polarographical dual wave) with the voltage gain of 400 mV/min. It is a cathode polarization, anode can be formed by a silver wire. From the wave amplitude the wave amplitude of the reference test is to be subtracted. The reference test uses solution of trivalent cobalt (by Brdicka) within the range of 1.3-1.45V.

The obtained values are marked in the following way:

$V_S$ = amplitude of the polarographical wave of the serum (test tube marked S) after the amplitude of the reference test wave has been subtracted.

$V_{E300}$ = amplitude of the polarographical wave of E$_{300}$ eluate after the amplitude of the reference test wave has been subtracted $V_{E500}$ = amplitude of the polarographical wave of E$_{500}$ eluate after the amplitude of the reference test wave has been subtracted $V_{norm}$ = average $V_S$ amplitude of a polarographical wave of the scrum of a blood donor The following relations define polarographical indexes of the serum and of its two eluates marked by symbols BI, $^{BI}E_{300}$, $^{BI}E_{500}$:

$$BI = \frac{V_s}{V_{NORM}} \quad BI_{E300} = \frac{V_{E300}}{V_{NORM}} \quad BI_{E500} = \frac{V_{E500}}{V_{NORM}}$$

For practical applications two more quantities are used, i.e. percentual polarographical indexes of E$_{300}$ and E$_{500}$ eluates that are defined by the following relations:

$$\%E_{300} = \frac{BI_{E300}}{BI} \times 100\%$$

$$\%E_{500} = \frac{BI_{E500}}{BI} \times 100\%$$

The serum and its two eluates are now specified by three polarographical indexes B, %E$_{300}$ and %E$_{500}$ that can be illustrated within a three dimensional vectorial space given by the beginning 0=[0, 0, 0,] and by three axes marked BI (z axis), %E$_{300}$(y axis) and %E$_{500}$ (x axis) by a point X=[BI, %E$_{300}$, %LE$_{500}$] or by a vector X=(BI, %E$_{300}$, %E$_{500}$) as it can be seen on FIG. 1.

BRIEF DESCRIPTION OF THE FIGURES

FIG. 1 illustrates the monitoring result represented by three polarographical indexes BI, %E$_{300}$ and %E$_{500}$. On the figure, applicable sections are defined on the axes x, y, z, by points A =[0, 0, 100], B =[0, 100, 0] and C=[2$_1$, 0, 0]. The X point is obtained by means of $\overline{OA^1}$, $\overline{OB^1}$ and $\overline{OC^1}$ segments, while the A$^1$, B$^1$, and C$^1$ points have their coordinates of [0, 0, %E$_{500}$], [0, %E$_{300}$, 0] and eventually [BI, 0, 0].

For calibration of the three dimensional space, four groups of persons with a known diagnosis have been used:

(1) group of normal healthy people (N)

(2) group of patients suffering from chronic inflammatory diseases (CH)

(3) group of patients suffering from acute inflammatory diseases (A)

(4) group of patients suffering from malignant growths diseases (M).

Figure 1:
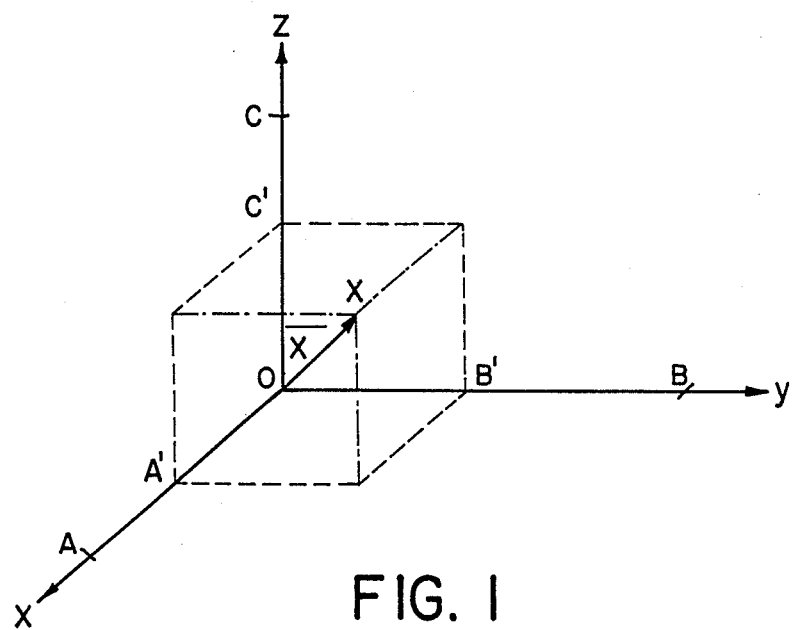
FIG. 1 shows monitoring results by three polarographical indexes.

Each of the groups consisted of 80-120 persons. Characteristic feature of the N groups is a very low BI index (BI <1.1), of the CH group a slightly increased BI index and low $\%E_{300}$ and $\%E_{500}$ indexes, of the A group an increased $\%E_{300}$ index and of the M groups in increased $\%E_{500}$ index. Individual clusters can be separated by boundary areas. The resulting situation is illustrated on FIG. 2, where the x, y, and z axes correspond to the x, y, and z axes on FIG. 1.

Figure 2:
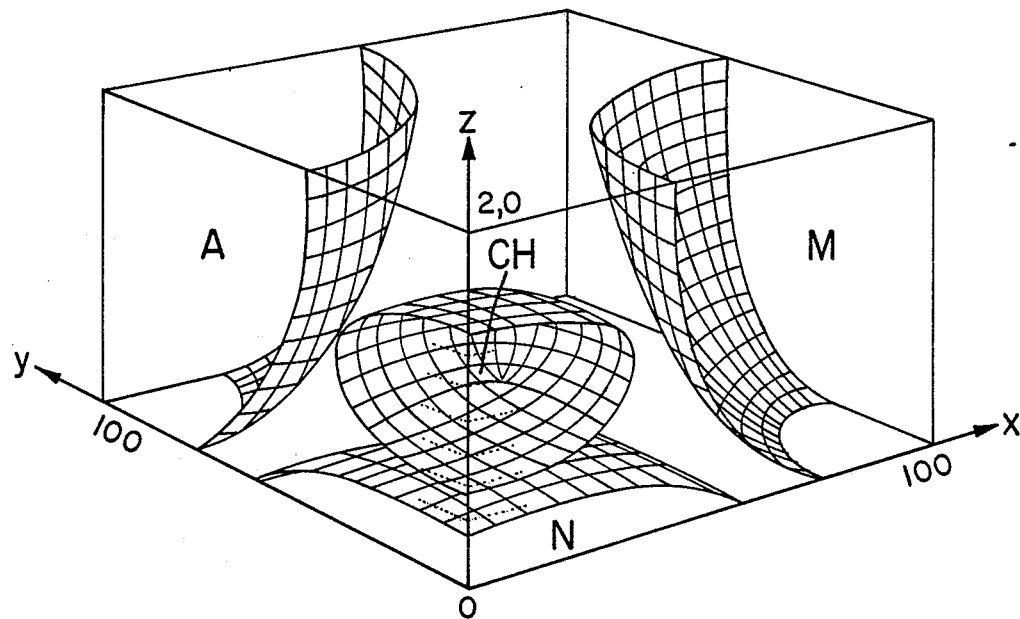
FIG. 2 shows calibration of a three dimensional space.

FIG. 2 illustrates calibration of the three-dimensional space by means of groups of persons with various diagnoses:

A=space for the group of patients suffering from acute inflammatory diseases

CH=space for the group of patients suffering from chronic inflammatory disease

N=space for the group of normal healthy people

M=space for the group of patient suffering from malignant growths.

The x axes indicates the $\%E_{500}$ values, y axis the $\%E_{300}$ values and the z axis the BI values.

The knowledge of parameters of individual clusters facilitates, on the basis of analysis of the mucoprotein serum, (in this case a polarographical analysis performed under identical conditions as stated above) to determine, which of the four groups—N, CH, A, M—the examined person belongs to.

Preferred Embodiment Of Separating Mucoproteins By Photometry

EXAMPLE II

Composition and preparation of solutions:

1. 50 mmol/l basic tris buffer, ph value, adapted by HCL, concentration to 7.0.
2. Eluting solution A: 40-50 mmol/l NaCl solution in basic tris buffer.
3. Eluting solution B: 320-330 mmol/l NaCl solution in basic tris buffer.
4. Eluting solution C: 480-510 mmol/l NaCl solution in basic tris buffer.
5. Sephadex Deae A-50 Gel: As much substance is weighed into the basic tris buffer so that after swelling about 0.5 cm free liquid remains over the Gel layer. To be prepared 24 hours in advance before use. Can be stored for about 14 days.
6. Physiological solution.
7. 1.8 mol/l perchloric acid.
8. 5% wolframophosphoric acid in 2N HCl.
9. Phenol reagents by flin-ClOCalteaud diluted before use with distilled water in 1:2 ration (procedure worked out Homolka, *Klinicka Bioch. Vysetr. Metody,* SZN 1969, Page 399).
10. 1/5 satured $Na_2CO_3$ solution: saturated $Na_2CO_3$ solution is prepared first, then it is filtered and diluted with distilled water in a 1:4 ration).
11. Stock standard solution: 20 mg tyrosin is dissolved 1/5 saturated $Na_2CO_3$ solution is added to make up 100 ml.
12. Standard solution: to 1 ml stock standard solution 1/5 saturated $Na_2CO_3$ solution is added to make up 10 ml.

Method Using Solutions Of Example II

A plastic column (5 ml syringe sealed with a cotton wad) is filled with 3.5ml gel. The column is sealed and adjusted in such a way that 9-12 drops/minute drip during washing with buffer A. The columns is carefully washed with 2 ml eluting solution A. After the last drop, 0.5 ml serum to the examined is pipetted onto the surface and is allowed to soak. Then 1.0 ml eluting solution A is pipetted into the column and is allowed to flow through. Then another 3 ml eluting solution A is pipetted. After the last drop, eluate A is obtained, which is used for selective preparation of B and C eluates. A beaker is now placed under the column (marked eluate B) and on top of the column 1 ml eluting solution B is pipetted first. After it has flown through the column, another 2.5 ml elutin solution B is added. After the last drop, eluate B is obtained. Then a beaker marked eluate C is put under the column and the whole procedure is repeated, this time with the eluting solution C. For further processing eluates B and C are used.

Further Procedure 0.25 ml serum to be examined is pipetted into a test tube marked S. 1.5 ml eluate B and C are pipetted into the test tubes marked B and C. 2.25 ml physiological solution is added into the test tube marked S and 1.0 ml physiological solution is put into the test tubes marked B and C. Contents of the three test tubes are stirred thoroughly, and into each of them 1.25 ml $HClO_4$ is added. The contents are stirred thoroughly again, left standing for 5 minutes. Then 2.5 ml supernatant is pipetted into other test tubes marked again S, B, and C. Supernatant is to be pipetted very carefully so as not to stir up the sedimented proteins. 0.5 ml 5% solution of wolframophosporic acid is added, stirred thoroughly, left standing for 5 minutes and centrifuged at 5.000 r.p.m. for 10 minutes. Then the supernatant is decanted, the test tubes are turned upside down, and the rims are dried with filter paper. 3.25 ml 1/5 saturated $NA_2CO_3$ solution is added into each of the test tubes and stirred thoroughly until the glycoprotein precipitate dissolves. Finally, 0.5 folin-CIOC. Reagens (see solution no.9) is added into each of the test tubes and the contents stirred thoroughly.

Blank Test:

3.25 ml 1/5 saturated $NA_2CO_3$ solution is mixed with 0.5 ml folin-CIOC. 7Reagens.

Processing of the standard solution: (see solution no.12).

0.5 ml standard solution is mixed with 2.75 ml 1/5 saturated $NA_2CO_3$ solution and 0.5 folin-CIOC.-Reagens.

All the test tubes must be stirred thoroughly (test, blank test, standard) and then must be kept for 45 minutes in the dark.

Photometry:

After 45 minutes—600 nm 1 cm Cuvette - test and standard against the blank test.

Calculation $$\frac{\text{Absolute value of the test}}{\text{Absolute value of the standard}} \times 6 = MG \text{ percent } mpt$$

From the calculations three results are obtained (test+2 eluates). They are processed by means of cluster analysis with a special computing program, respectively from nomograms.

Summary Of The Use Of The Presently Claimed Invention

When diagnosing treated and untreated malignant growths, (the rate between treated and untreated persons was within the limits of general examinations carried out in biochemical laboratories), "false" negativity was discovered in about 10% case. Mostly they were cases when malignant growths were in advanced stages where regressive changes had taken place, which leads to an increase in the inflammatory %$E_{300}$ component in the blood serum. Thus, those conditions are usually evaluated as acute inflammations. But in that stage, monitoring of the patient is no more necessary since the main contribution of the described method lies in discovering malignant growths before they manifest themselves clinically.

Successfully treated malignant growth produce generally results within the space of chronic inflammatory processes. It is possible to monitor permanently those patients and thus to check the efficiency of their treatment.

False positivity has occurred very rarely only. Practically, they were few cases of children suffering from some inflammatory diseases and the result obtained by our method indicated malignant growths.

From the results obtained so far the verified reliability of the described method amounts to some 90%. The method opens up new possibilities for diagnosing malignant growth in their early stages—without specifying their type and location. The method also offers the possibility to check efficiency of the treatment of malignant growth by means of classic methods.

Although the invention is described and illustrated with reference to a number of embodiments thereof, it is to be expressly understood that it is in no way limited to the disclosure of such preferred embodiments but is capable of numerous modifications within the scope of the appended claim.

We claim:

1. A method for determining a mucoprotein vector of blood serum mucoproteins, and its eluates obtained through separation, by means of ion-exchanger, comprising the steps of separating the blood serum mucoproteins in the mucoprotein components of blood into at least two subgroups by means of gel ion-exchanger chromatography;

determining individual mucoprotein polarographical indexes in the two subgroups and in the whole serum; and then transferring each individual mucoprotein polargraphical index Bl, $E_{300}$, and $E_{500}$ to x, y, and z axes, wherein on one of said axes is plotted one subgroup, on a second one of said axes is plotted another subgroup, and on a third one of said axes is plotted the whole serum;

wherein a point corresponding to the mucoprotein vector, specific for the given blood, is otained, and wherein the mucoprotein vector values are classified according to the state of health of donors of the above mentioned blood serum so that diagnostic decisions may be taken.

* * * * *